United States Patent [19]

Chen et al.

[11] Patent Number: 5,393,912
[45] Date of Patent: Feb. 28, 1995

[54] D-MYO-INOSITOL 1,4,5-TRISPHOSPHATE ANALOGUES

[75] Inventors: Ching-Shih Chen, Wakefield; Da-Ming Gou, Kingston; Woan-Ru Shieh, Wakefield, all of R.I.

[73] Assignee: The Board of Governors for Higher Education, State of Rhode Island and Providence Plantations, Providence, R.I.

[21] Appl. No.: 181,188

[22] Filed: Jan. 13, 1994

[51] Int. Cl.⁶ .................................. C07F 9/117
[52] U.S. Cl. ........................................ 558/161
[58] Field of Search ........................... 558/161

[56] References Cited

U.S. PATENT DOCUMENTS

| | | | |
|---|---|---|---|
| 4,873,355 | 10/1989 | Hobbs et al. | 558/161 |
| 5,210,263 | 5/1993 | Kozikowski et al. | 558/161 |
| 5,260,472 | 11/1993 | Chen | 558/161 |
| 5,292,913 | 3/1994 | Ozaki et al. | 558/87 |

*Primary Examiner*—Mary C. Lee
*Assistant Examiner*—Michael G. Ambrose
*Attorney, Agent, or Firm*—Samuels, Gauthier & Stevens

[57] ABSTRACT

Two types of structural analogues of D-myo-inositol 1,4,5-trisphosphate [Ins(1,4,5)P₄] are prepared by a chemo-enzymatic route. These 6-O-substituted analogues retain the biological activity of Ins(1,4,5)P₃ and are able to elicit $Ca^{2+}$ release from porcine brain microsomes. Moreover, these analogues allow the preparation of Ins(1,4,5)P₃-based immunogens and affinity matrix which are successfully applied to the preparation and purification of antibodies against Ins(1,4,5)P₃. These antibodies display discriminative affinity toward Ins(1,4,5)P₃, and provide a useful tool to study intracellular $Ca^{2+}$ mobilization.

2 Claims, 2 Drawing Sheets

D-MYO-INOSITOL 1,4,5-TRISPHOSPHATE ANALOGUES

BACKGROUND AND BRIEF SUMMARY OF THE INVENTION

D-myo-inositol 1,4,5-trisphosphate [Ins(1,4,5)P$_3$] is generated from the phospholipase C-mediated breakdown of membrane phosphatidylinositol 4,5 bisphosphate [PtdIns(4,5)P$_2$] in response to stimulation by hormones, neurotransmitters, and growth factors, Berridge, M. J., *Nature*, 1993, 361, 315, and references cited therein. Ins(1,4,5)P$_3$, in turn, elicits Ca$^{2+}$ mobilization and, subsequently, an array of intracellular events by interacting with specific receptors on intracellular organelles, Meldolesi, J.; Villa, A.; Volpe, P.; Pozzan, T., *Advanced in Second Messanger and Phosphoproein Research*; Putney, J. W., Jr., Ed.; Raven Press: New York, 1992; Vol. 26, pp 187–208. While many researchers assert that the biologically relevant receptors for Ins(1,4,5)P$_3$ distribute mainly on the membrane of the endoplasmic reticulum or nucleus, others suggest the locality on a more specialized endomembrane fraction, i.e., calciosomes, Volpe, P.; Kraus, K. H.; Sadamitsu, H.; Zorzato, F.; Pozzan, T.; Meldolesi, J.; Low, P. B., *Proc. Natl. Acad. Sci, USA*, 1988, 85, 1091. In the second phase of the signaling process, i.e., Ca$^{2+}$ entry from the extracellular medium, Ins(1,4,5)P$_3$ has also been implicated. The capacitative entry theory suggests that depletion of the intracellular Ca$^{2+}$ store by Ins(1,4,5)P$_3$ generates a secondary signal of unknown nature that activates Ca$^{2+}$ entry, Putney, J. W., Jr., *Cell Calcium*, 1986, 7, 1; Takemura, H.,; Putney, J. W., Jr., *Biochem. J.*, 1989, 258, 409; Putney, J. W., Jr., *Advances in Second Messanger and Phosphoprotein Research*; Putney, J. W., Jr., Ed.; Raven Press: New York, 1992; Vol. 26, pp 143–160. Thus, the mechanism of interaction between the Ins(1,4,5)P$_3$-sensitive Ca$^{2+}$ pool and the Ca$^{2+}$ channel on plasma membrane (Ins(1,4,5)P$_3$-mediated Ca$^{2+}$ homeostasis) has not yet been satisfactorily resolved.

The present invention embodies novel Ins(1,4,5)P$_3$ analogues and the syntheses for such analogues. Although a number of Ins(1,4,5)P$_3$ analogues have been reported, the reactive appendages of these derivatives were attached to the parent molecule through a C-1 phosphodiester linkage, Prestwich, G. D.; Marecek, J. F.; Mourey, R. J.; Theibert, A. B.; Ferris, C. D.; Danoff, S. K.; Snyder, S. H., *J. Am. Chem. Soc.*. 1991, 113, 1822; Tegge, W.; Ballou, C. E., *Carbohydr. Res.*, 1992, 230, 63. The present invention, in a preferred embodiment, is directed to the synthesis of two novel Ins(1,4,5)P$_3$ analogues, 1 and 2, with modification at the C-6 position.

The derivatized Ins(1,4,5)P$_3$ contains an amine or aldehyde function for further elaborations which allows the preparation of Ins(1,4,5)P$_3$-based analogues for antibody induction, affinity purification, and histochemical probing.

DESCRIPTION OF THE PREFERRED EMBODIMENT(S)

In light of the delicate structure of Ins(1,4,5)P$_3$, the latitude in the choice of a site(s) for modification is limited. The design of these two optically active Ins(1,4,5)P$_3$ analogues, 1 and 2, was based on (a) the strategic importance of the C-2,3 cis-dihydroxy moiety, especially the axial 2-OH, in recognizing Ins(1,4,5)P$_3$ versus other inositol phosphates, and (b) the intactness of the three phosphate functions in derivatized Ins(1,4,5)P$_3$ to achieve optimal ionic interactions with the binding proteins.

Both 1 and 2 were synthesized from (+)-2,3:4,5-di-O-cyclohexylidene-D-myoinositol, (+)-3, through similar routes.

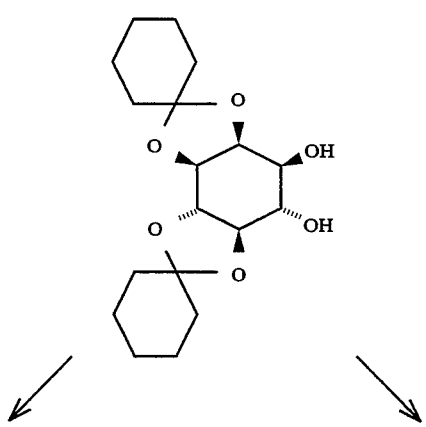

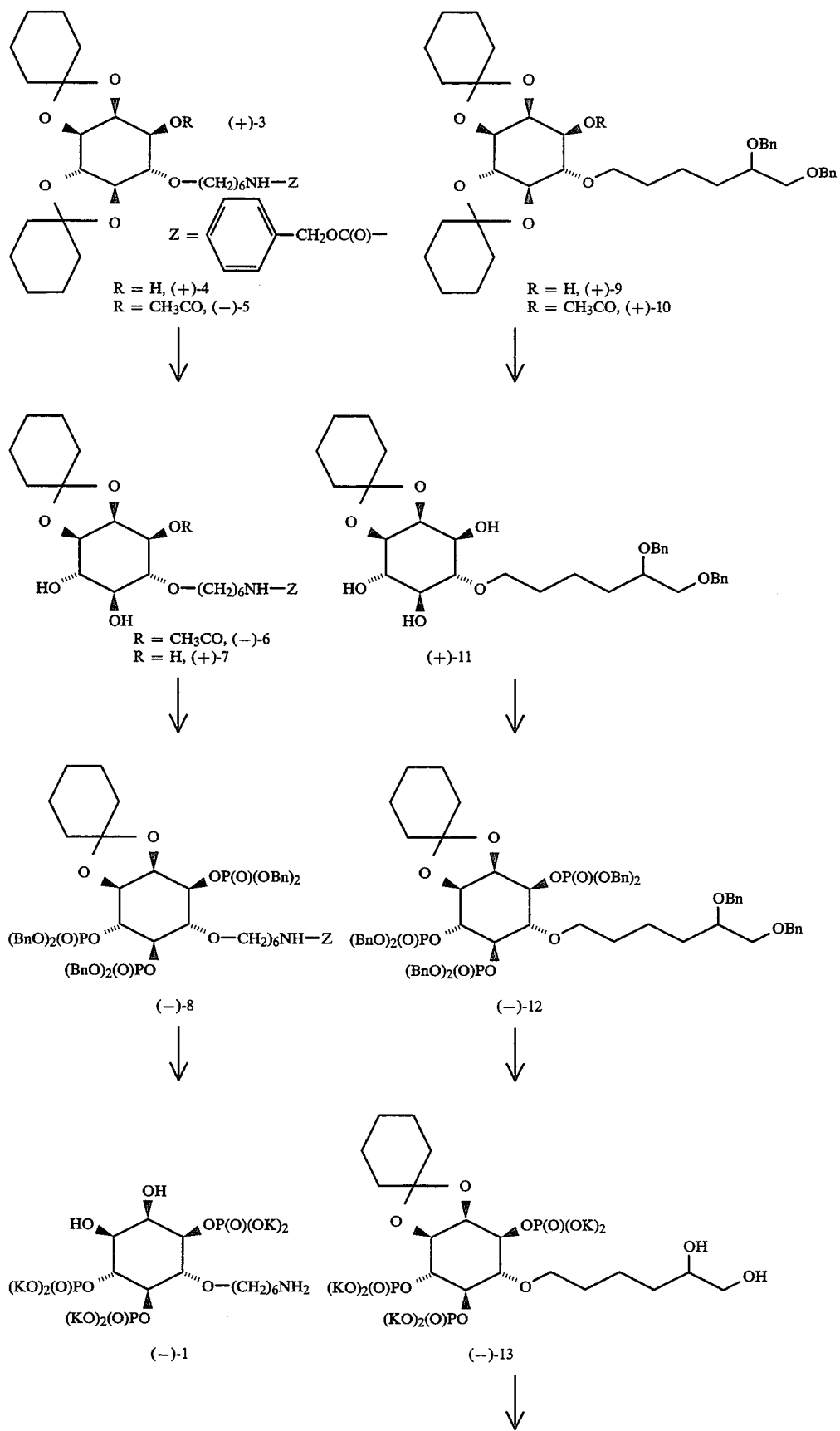

-continued

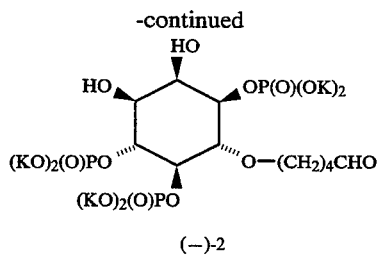

(−)-2

The chiral precursor was prepared by enantioselective hydrolysis of its ratemic 6-O-butyryl ester by porcine pancreatic lipase Gou, D.-M; Liu, Y.-C.; Chen, C.-S., Carbohydr. Res., 1992, 234, 51. The stannylidene-activated alkylation allowed the regioselective introduction of the substituents at the 6-O position to afford (+)-4 and (+)-9 in good yields. To prevent acid-catalyzed migration of the cis-cyclohexylidene group under acidic conditions, 4 and 9 were acetylated to give (−)-5 and (+)-10, respectively, methanolysis of which removed the trans-cyclohexylidene ring and saponification of the products furnished (+)-7 and (+)-11, respectively. Phosphorylation of the triol 7 by the phosphoramidite method, Yu, K.-L.; Fraser-Reid, B., Tetrahedron Lett, 1988, 29, 979, followed by debenzylation and acid hydrolysis of the cisketal, gave the trisphosphate (−)-1. Similar treatments of 11 but without the acid hydrolysis led to (−)-13. The overall yields for the synthesis of 1 and 13 from (+)-3 were 37% and 45%, respectively. These two compounds were fully characterized by $^1H$ and $^{31}P$ NMR and mass spectrometry. The aldehyde-bearing derivative (−)-2 was readily afforded by subjecting the vicinal diol 13 to periodate oxidation and a subsequent acid treatment.

With the functionalities of amine and aldehyde in the side arms, analogues 1 and 2 allows the coupling of Ins(1,4,5)P₃ to virtually any type of molecule. Moreover, the three phosphate functions of the resulting conjugates are fully exposed, resembling the charge state of the parent compound.

Figure 1:
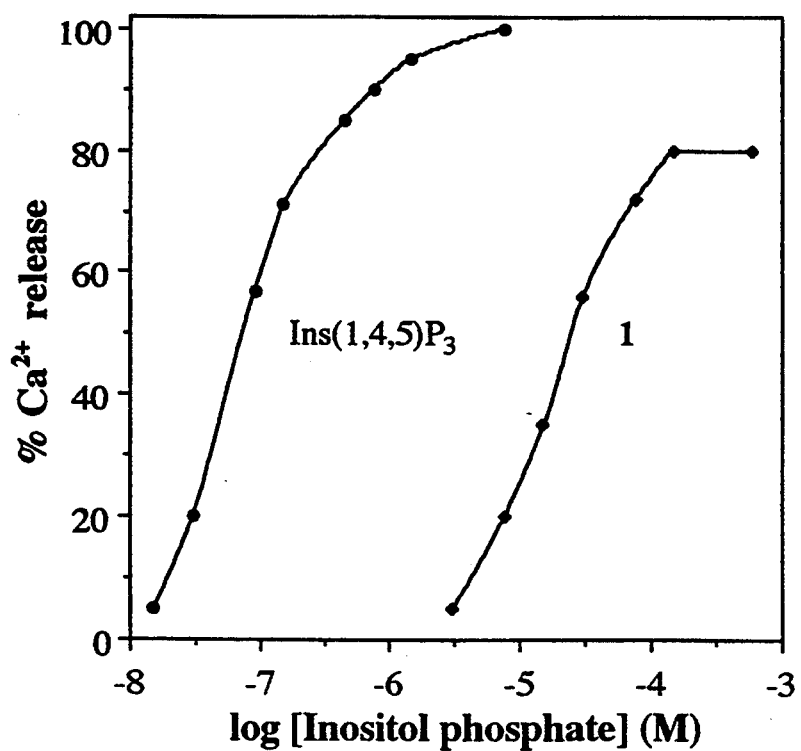
FIG. 1 is a graph of Ca$^{2+}$ releasing activity of Ins(1,4,5)P$_3$ versus analogue 1.

The derivatized Ins(1,4,5)P₃ retained the biological activity of Ins(1,4,5)P₃. For instance, 1 was able to mobilize 80% of Ins(1,4,5)P₃-sensitive $Ca^{2+}$ store when porcine brain microsomes were saturated. Referring to FIG. 1, $Ca^{2+}$-loaded porcine brain microsomes were treated with $Ca^{2+}$-mobilizing agents, and released $Ca^{2+}$ was monitored by a $Ca^{2+}$-sensitive fluorescent dye, Fura-2, according to the method described in the experimental section (100%=$Ca^{2+}$ release at saturated concentrations of Ins(1,4,5)P₃). Each data point represents the means of three determinations.

The $EC_{50}$ values were 79 nM and 18 μM for Ins(1,4,5)P₃ and 1, respectively. Although the $Ca^{2+}$-mobilizing activity of the analogue was about 200-fold less potent than that of the parent compound, it could interact functionally with the Ins(1,4,5)P₃-specific receptor(s) in the microsomes. The decrease in affinity was presumably due to the hydrophobic side arm which imposed steric and/or stereoelectronic effect(s) on binding. It has recently been reported that the 6-OH may have an important role in the interactions with receptors and metabolis enzymes, Hirata, M.; Watanabe, Y.; Yoshida, M.; Koga, T.; Ozaki, S., J. Biol. Chem., 1993, 268, 19260; Kozikowski, A. P.; Ognyanov, V. I.; Fauq, A. H.; Nahorski, S. R.; Wilcox, R. A., J. Am. Chem. Soc., 1993, 115, 4429. The finding that these 6-O substituted analogues were active in $Ca^{2+}$ mobilization broadened the utility of these molecules, which is illustrated in the following two examples.

INDUCTION OF ANTIBODIES

An eminent application of these analogues was to prepare immunogens for raising Ins(1,4,5)P₃-specific antibodies. These anti-Ins(1,4,5)P₃ antibodies have important use in quantitative analysis of Ins(1,4,5)P₃ and as a biochemical probe to assess the role of Ins(1,4,5)P₃ in $Ca^{2+}$ mobilization.

Both 1 and 2 could be coupled to carrier proteins by conventional methods. The amine-bearing derivative 1 was cross-linked to bovine serum albumin (BSA) using glutaraldehyde as a coupling agent followed by in situ $NaBH_4$ reduction to afford IP₃-C₆NC₅-BSA. The aldehyde 2 formed a shiff base with the amino functions of BSA, which yielded the conjugate IP₃-C₅-BSA upon $NaBH_4$ reduction. The molar ratios of the bound Ins(1,4,5)P₃ to BSA were estimated to be 22 and 5 for IP₃-C₆NC₅-BSA and IP₃C₅-BSA, respectively, according to the phosphorus contents. The distance between the coupled Ins(1,4,5)P₃ and the carrier protein was 19.7 Å and 9 Å, respectively.

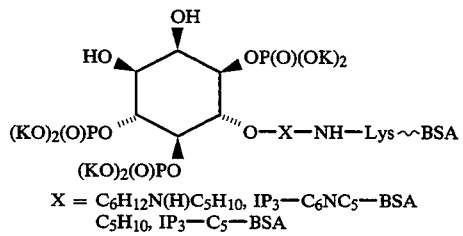

X = $C_6H_{12}N(H)C_5H_{10}$, IP₃—C₆NC₅—BSA
$C_5H_{10}$, IP₃—C₅—BSA

Both Ins(1,4,5)P₃-BSA conjugates were used to induce antibodies in New Zealand rabbits. After receiving 2–3 booster injections, rabbits receiving either antigen were found to produce antibodies with titers of 1:4,000.

Figures 2A, 2B:
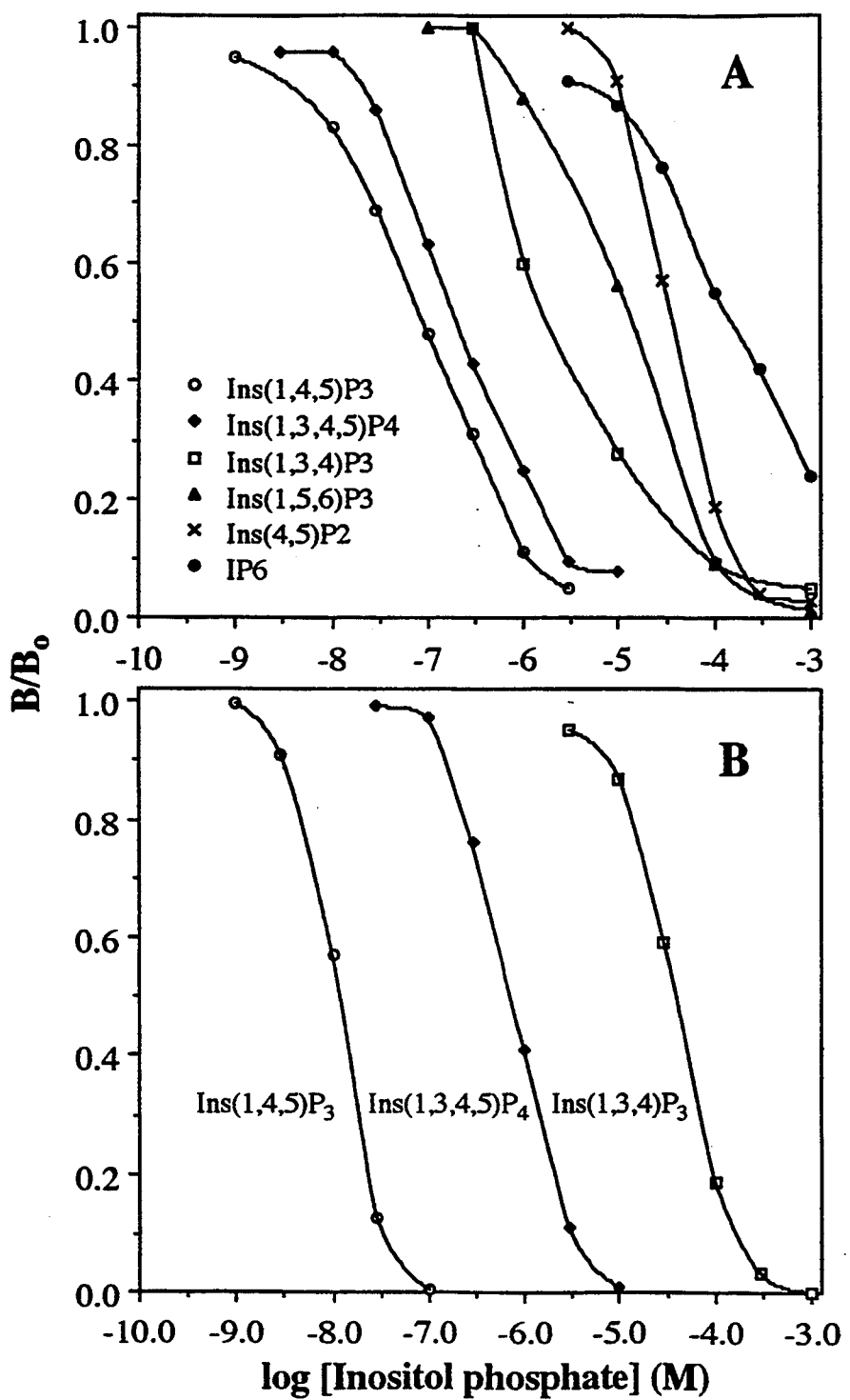
FIGS. 2a and 2b are graphs of the inositol phosphate specificity of (A) crude rabbit serum and (B) affinity-purified antibodies.

Referring to FIG. 2a and b, the displacement curves were generated from competitive ELISA experiments between immobilized Ins(1,4,5)P₃ and various inositol phosphates shown in the insert. Percentage total specific binding is expressed by B/B$_o$, where B=absorbance with competitor and B$_o$=absorbance without competitor. Each data point represents the means of three determinations. The avidity and specificity of these antisera appeared to be independent of the spacer length and IP₃ content of the antigens. The affinity toward different inositol phosphates was in the order of: Ins(1,4,5)P₃ > Ins(1,3,4,5)P₄ > Ins(1,3,4)P₃ > Ins(1,5,6)P₃ > Ins(4,5)P₂ > IP₆ (FIG. 3A). The degree of discrimination between Ins(1,4,5)P₃ and Ins(1,3,4,5)P₄ by these antisera appeared to be lower than that reported for Ins(1,4,5)P₃ receptors, Wilcox, R. A.; Challiss, R. A. J.; Baudin, G.; Vasella, A.; Potter, B. V. L.; Nohorski, S. R., Biochem. J., 1993, 294, 191, which may be accounted for by the heterogeneity in the antigen binding sites. To remove the less specific antibodies, the antiserum was subjected to affinity chromatography on Ins(1,4,5)P$_3$-agarose.

AFFINITY PURIFICATION

The affinity matrix was prepared by reacting 1 with 1,1'-carbonyldiimidazole-activated agarose (Reacti-Gel(®); Pierce). The Ins(1,4,5)P$_3$-specific antibodies displayed strong binding with the affinity matrix, and could only be eluted under alkaline conditions (100 mM NaHCO$_3$/Na$_2$CO$_3$ buffer, pH 10.5). These affinity purified antibodies showed much improved selectivity between Ins(1,4,5)P$_3$ and Ins(1,3,4,5)P$_4$ with IC$_{50}$ of 12 nM and 730 nM, respectively. The differential affinity, as indicated by the ratios of IC$_{50}$ values, increased from 2- to 60-fold. The degree of specificity for these affinity purified antibodies was in line with that reported for Ins(1,4,5)P$_3$-specific receptors, Wilcox, R. A.; Challiss, R. A. J.; Baudin, G.; Vasella, A.; Potter, B. V. L.; Nohorski, S. R., *Biochem. J.,* 1993, 294, 191. Moreover, the span of inositol phosphate concentrations for complete displacement decreased from 3 log-units to 1 unit, indicating improved specificity of the purified antibodies. Application of this affinity matrix to the purification of the biologically relevant receptors is currently under investigation.

EXPERIMENTAL SECTION

General Methods $^1$H, $^{13}$C, and $^{31}$P NMR spectra were recorded with a Bruker AM300 spectrometer. Optical rotations were determined at 23° C. with a Rudolph Autopol III polarimeter. Fast atom bombardment mass spectra (FAB-MS) were obtained from the Chemical Instrument Center, Yale University. Elemental analysis was performed by MH-W laboratories (Phoenix, Ariz.). Fluorescence spectrophotometric assay of Ca$^{2+}$ release was carried out with a Hitachi F-2000 spectrometer.

Materials. (1,4,5)IP$_3$, (1,3,4)IP$_4$, and (1,3,4,5)IP$_4$ were synthesized from optically active 1,2:5,6-di-O-cyclohexylidene-inositol 1 (optical purity >98% enantiomeric excess) according to previously described procedures, Gou, D.-M; Liu, Y.-C.; Chen, C.-S., *Carbohydr. Res.,* 1992, 234, 51; Liu, C.-Y.; Chen, C.-S., *Tetrahedron Lett.,* 1989, 30, 1617; Gou, D.-M.; Chen, C.-S.;, *Tetrahedron Lett.,* 1992, 33, 721. (4,5)IP$_2$, (1,5,6)IP$_3$ were prepared by following a similar approach with pertinent modifications. The chemical purity of these chiral inositol phosphates was greater than 95% according to $^1$H and $^{31}$P NMR spectroscopy. The amount of isomeric impurities was negligible as indicated by these NMR spectra. Phytic acid was purchased from Sigma.

(+)-6-O-(ω-Benzyloxycarbonylaminohexyl)-2.3:4,5-di-O-cyclohexylidene-myo-inositol 4-A mixture of (+)-2,3:4,5-di-O-cyclohexylidene-D-myo-inositol 3 (1 g, 2.9 mmol), Bu$_2$SnO (840 mg, 3 mmol), and toluene (25 ml) was boiled under reflux with azeotrophic removal of water for 1 h, then concentrated to dryness under reduced pressure. To the residue were added N,N-dimethylformamide (10 ml) and benzyloxycarbonylaminohexyl bromide (2 g, 8.5 mmol). The mixture was stirred at 23° C. overnight, then diluted with CH$_2$Cl$_2$ (50 ml), washed with saturated aq. NaCl, dried with Na$_2$SO$_4$, and concentrated. Column chromatography of the residue on a silica gel column (hexane-ether, 15:1) gave 4 (1.1 g, 65%). [α]D +4°-9° (c 1.7, CHC13). $^1$H NMR (CDCl$_3$) δ 1.25–1.71 (m, 28H), 2.66 (d, 1H, J=1 Hz), 3.14–3.21 (m, 2H), 3.40–3.48 (m, 1H), 3.50–3.59 (m, 1H), 3.63–3.73 (m, 2H), 3.93–3.94 (m, 1H), 4.12–4.18 (m, 1H), 4.32 (t, 1H, J=6 Hz), 4.37–4.41 (m, 1H), 4.86 (m, 1H), 5.08 (s, 2H), 7.28–7.35 (m, 5H); 13C NMR (CDCl$_3$) δ 15.16, 23.37, 23.65, 23.73, 25.03, 25.09, 25.69, 26.42, 29.59, 29.87, 33.52, 36.35, 36.57, 36.67, 41.07, 53.28, 65.69, 66.53, 69.78, 72.35, 75.34, 76.74, 77.19, 78.19, 78.84, 80.40, 111.17, 112.71, 127.96, 128.42, 136.79, 156.39.

(−)-1-O-Acetyl 6-O-(ω-benzyloxycarbonylaminohexyl)-2,3-O-cyclohexylidene-myoinositol 6-A solution of 4 (1 g, 1.7 mmol) in CH$_2$Cl$_2$ (10 ml) was treated with acetic anhydride (0.4 ml, 3.5 mmol), and 4-dimethylaminopyridine (208 mg, 1.7 mmol) at 23° C. for 30 min. The mixture was washed with aq. NaHCO$_3$ and water, dried, and concentrated to afford (−)-1-O-acetyl-6-O-(benzyloxycarbonylaminohexyl)-2,3:4,5-di-O-cyclohexylidene-myo-inositol 5 (syrup) in quantitative yield. 13C NMR (CDCl$_3$) δ 13.97, 15.18, 21.10, 22.57, 23.49, 23.70, 23.87, 25.03, 25.09, 25.65, 26.42, 29.54, 29.89, 31.52, 34.27, 36.47, 36.63, 41.12, 64.10, 65.72, 66.54, 70.01, 72.81, 73.41, 77.19, 78.38, 79.75, 111.62, 113.02, 127.99, 128.45, 136.86, 156.41, 169.43. A solution of the oily compound in CH$_2$Cl$_2$-CH$_3$OH (1:1, 10 ml) was stirred with acetyl chloride (0.1 ml, 1.2 mmol) at 23° C. for 10 min. Triethylamine (0.3 ml) was added, and the solution was concentrated. Column chromatography (hexane-ether, 20:1) of the residue yielded (−)-6 (syrup, 0.67 g, 75%). [α]D −14.8° (c 1.1, CHCl$_3$). $^1$H NMR (CDCl$_3$) δ 1.30–1.72 (m, 18H), 2.14 (s, 3H), 3.15–3.21 (m, 2H), 3.33–3.39 (m, 1H), 3.44–3.51 (m, 2H), 3.56 (t, 1H, J=9 Hz), 3.64–3.78 (m, 3H), 4.01–4.05 (m, 1H), 4.39–4.42 (m, 1H), 4.85 (m, 1H), 5.03–5.09 (m, 3H), 7.30–7.36 (m, S H); 13C NMR (CDCl$_3$) δ 13.97, 15.16, 21.02, 23.56, 23.97, 25.03, 25.65, 26.35, 29.85, 29.97, 34.99, 37.58, 66.67, 71.64, 72.48, 73.17, 73.70, 74.92, 77.19, 78.30, 79.49, 110.97, 113.02, 127.99, 128.04, 128.50, 156.52, 170.02.

(+)-6-O-(ω-benzylocycarbonylaminohexyl)-2,3-O-cyclohexlidene-myo-inositol 7-The acetate 6 (0.9 g, 1.7 mmol) was treated with methanolic 1M NaOH for 1 h at 23° C., and the solvent was evaporated under reduced pressure. Column chromatography (hexane-ether, S: 1) of the residue afforded (+)-7 (0.77 g, 93%). [α]D +11.6° (c 2.4, CHCl$_3$). $^1$H NMR (CDCl$_3$) δ 1.34–1.72 (m, 18H), 2.84 (br. s, 1H), 3.13–3.20 (m, 2H), 3.30–3.35 (m,1H), 3.44–3.51 (m, 2H), 3.69–3.85 (m, 5H), 3.99–4.03 (m, 1H), 4.34–4.37 (m, 1H), 5.01 (br. s, 1H), 5.08 (br. s, 2H), 7.27–7.35 (m, 5H); 13C NMR (CDCl$_3$) δ 23.61, 24.03, 25.08, 25.66, 26.38, 29.88, 30.00, 34.75, 37.52, 41.07, 66.71, 70.47, 72.16, 74.04, 75.08, 75.26, 77.10, 78.29, 81.90, 110.73, 128.09 (2C), 128.54 (2C), 136.83, 156.64.

6-0-(ω-benzyloxycarbonylaminohexyl)-2,3-0-cyclohexylidene-myo-inositol 1,4,5-tris-(dibenzyl phosphate) 8-A mixture of 1H-tetrazole (2.5 g, 35 mmol), dibenzyl N,N-di-isopropylphosphoramidite (6 g, 7 mmol), and CH$_2$Cl$_2$ (40 ml) was stirred under Ar at 23° C. for 1 h, and (+)-7 (0.75 g, 1.5 mmol) was added in one portion. The solution was kept under the same conditions for another 12 h, cooled to −15 ° C., and then treated with m-chloroperoxybenzoic acid (50% purity, 7 g, 17 mmol). The mixture was stirred at −15° C. for 30 min, then allowed to attain room temperature, diluted with CH$_2$I$_2$ (80 ml), washed with aq. Na$_2$SO$_3$, aq. NaHCO$_3$, and water, dried, and concentrated. Column chromatography (hexane-ether, 15:1) of the residue furnished (−)-8 (syrup, 1.6 g, 83%). [α]$_D$ −3.4° (c 3, CHCl$_3$). $^1$H NMR (CDCl$_3$) δ 1.11–1.74 (m, 18H), 3.08

(q, 2H, J=6.5 and 12.9 Hz), 3.43–3.48 (m, 1H), 3.54–3.60 (m, 1H), 3.97 (q, 1H, J=5.4 and 7.8 Hz), 4.24 (t, 1H, J=6.6 Hz), 4.48–4.58 (m, 2H), 4.67–4.74 (m, 1H), 4.87–5.10 (m, 16H), 7.20–7.32 (m, 35H);

(−)6-O-(ω-aminohexyl)-D-myo-inositol 1,4,5-triphosphate 1-A solution of (−)-8 (1.5 g, 1.2 mmol) in aq. 80% ethanol was shaken under $H_2$ (50 psi) in the presence of 10% Pd/C (0.5 g) for 15 h, then filtered, and concentrated to dryness. To the residue was added 2 ml of glacial acetic acid, and the resulting solution was stirred at 23° C. for 2 h, and concentrated. The residue was triturated with $CH_2Cl_2$-ether (1:1), the resulting white precipitate was dissolved in the minimum amount of water, and 1M KOH (6 equiv.) was added. The solution was lyophilized to afford 1 as the hexapotassium, acetate salt (0.92 g, 99%). $[\alpha]_D$ −14° (c 1.1, $H_2O$). $^1H$ NMR ($D_2O$) δ 1.10–1.23 (m, 4H), 1.23–1.38 (m, 2H), 1.40–1.53 (m, 2H), 2.48 (br. s, 2H), 3.43–3.72 (m, 4H), 3.91–4.14 (m, 4H); $^{31}P$ NMR ($D_2O$, external $H_3PO_4$, broadband decoupled): 2.28, 2.64, and 3.18. FAB-MS m/q 790 [$C_{12}H_{22}NO_{15}P_3K_6$ (M)-H2O], 752 M-K+1H], 714 [M-2K+2H], 672 [M-2K-HOAc+2H], 591 [M-P(O)(OK)_2].

(+)-6-O-(5′,6′-dibenzyloxyhexyl)-2:3,4:5-di-O-cyclohexylidene-myo-inositol 9-A mixture of 3 (1 g, 2.9 mmol), $Bu_2SnO$ (840 mg, 3 mmol), and toluene (30 ml) was boiled under reflux for 1 h, then concentrated to dryness under reduced pressure. To the residue were added N,N-dimethylformamide (10 ml), CsF (1.3 g, 8.6 mmol), and 5,6 dibenzyloxyhexyl bromide (2.5 g, 6.7 mmol). The mixture was stirred at 23° C. overnight, then diluted with ethyl acetate (50 ml), washed with saturated aq. NaCl, dried ($Na_2SO_4$), and concentrated. Column chromatography (hexane-ether, 15:1→5:1) of the residue gave 9 (syrup, 1.5 g, 80%). $[\omega]_D$ +3.8° (c 3, $CHC_3$). $^1H$ NMR ($CDCl_3$) 1.38–1.72 (m, 26H), 2.59–2.63 (m, 1H), 3.40–3.73 (m, 7H), 3.90–3.93 (m, 1H), 4.12–4.19 (m, 1H), 4.29–4.38 (m, 2H), 4.53–4.71 (m, 4H), 7.26–7.35 (m, 10H); $^{13}C$ NMR ($CDCl_3$) δ 22.08, 23.49, 23.77, 23.85, 23.94, 25.15, 25.21, 29.90, 31.88, 33.63, 36.47, 36.70, 36.79, 69.89, 72.05, 72.06, 72.46, 72.47, 73.09, 73.11, 73.48, 75.45, 76.87, 77.26, 78.27, 78.98, 79.00, 80.47, 111.28, 112.82, 127.46, 127.59, 127.64, 127.79, 128.31, 128.40. 138.61. 139.17.

(+)-6-O-(5′,6′-dibenzyloxyhexyl)-2:3-O-cyclohexylidene-myo-inositol 1 1-A solution of 9 (1.5 g, 2.3 mmol) in $CH_2Cl_2$ (15 ml) was treated with acetic anhydride (1.2 ml, 12.7 mmol) and 4-dimethylaminopyridine (1.6 g, 13 mmol) at 23° C. for 1 h. The mixture was washed with aq. $NaHCO_3$ and water, dried, and concentrated to afford 1-Oacetyl-6-O-(5′, 6′-dibenzoxyhexyl)-2:3-cyclohexylidene-myo-inositol (10) in quantitative yield. Without purification, the oily compound was dissolved in a solution of $CH_2Cl_2CH_3OH$ (1:1, 10 ml), and treated with acetyl chloride (0.1 ml, 1.4 mmol) for 10 min. Triethylamine (0.5 ml) was added, and the solution was concentrated. To the crude residue was added 1.2 equiv. of methanolic 1M NaOH. The solution was stirred at 23° C. for 1 h, and solvent was removed under reduced pressure. Column chromatography (hexane-ether, 10:1) of the residue afforded 11 (syrup, 0.91 g, 70%). $[\alpha]_D$ +9.9° (c 1.1, $CHCl_3$). $^1H$ NMR ($CDCl_3$) δ 1.30–1.74 (m, 16H), 2.80 (dd, 1H, J=4.8 and 60 Hz), 3.12–3.32 (m, 3H), 3.38–3.44 (m, 1H), 3.49–3.59 (m, 4H), 3.68–3.74 (m, 4H), 3.90–3.98 (m, 1H), 4.19–4.34 (m, 1H), 4.50–4.55 (m, 2H), 4.70 (dd, 1H, J=4.8 and 10 Hz), 7.26–7.34 (m, 10H); $^{13}C$ NMR ($CDCl_3$) δ 21.66, 21.71, 23.58, 23.99, 25.05, 29.92, 31.49, 34.81, 34.84, 37.56, 70.49, 71.94, 71.95, 72.17, 72.24, 72.91, 72.96, 73.48, 73.79, 75.19, 75.29, 78.20, 78.29, 81.49, 81.67, 127.60, 127.64, 127.69, 127.97, 128.04, 128.36, 128.41.

(−)-6-O-(5′,6′-dibenzyloxyhexyl)-2:3-O-cyclohexylidene-myo-inositol 1,4,5-tris (dibenzyl phosphate) 12-A mixture of 1H-tetrazole (2.75 g, 39 mmol), dibenzyl N,N-di isopropylphosphoramidite (7.49 g, 8.7 mmol), and $CH_2Cl_2$ (30 ml) was stirred under Ar at 23° C. for 1 h, and (+)-11 (0.89 g, 1.6 mmol) was added in one portion. The solution was kept under the same condition for another 12 h, cooled to 40° C., and then treated with m-chloroperoxybenzoic acid (50% purity, 9 g, 25 mmol). The mixture was stirred at −40° C. for 10 min, then allowed to attain room temperature, diluted with $CH_2Cl$ (80 ml), washed with aq. $Na_2SO_3$, aq. $NaHCO_3$, and water, dried, and concentrated. Column chromatography (hexane-ether, 15:1) of the residue furnished (−)-12 (syrup, 2 g, 93%). $[\alpha]_D$ −3° (c 1.1, $CHCl_3$). $^1H$ NMR data ($CDCl_3$): δ 1.25–1.91 (m, 16H), 3.38–3.60 (m, 5H), 3.98 (dd, 1H, J=4.8 and 6.0 Hz), 4.25 (t, 1H, J=6.6 Hz), 4.47–4.70 (m, 6H), 4.92–5.10 (m, 14H), 7.21–7.34 (m, 40H).

6-O-(5′,6′-dihyroxyhexyl)-2:3-O-cyclohexylidene-myo-inositol 1,4,5-triphosphate 13-A solution of 12 (0.2 g, 0.15 mmol), and 1M KOH (0.9 ml, 0.9 mmol) in aq. 80% ethanol was shaken under $H_2$ (50 psi) in the presence of 10% Pd/C (1 g) for 24 h, then filtered, and concentrated. The residue was dissolved in water (10 ml), and lyophilized to afford 13 as the hexapotassium salt (0.13 g, 99%). $^1H$ NMR data ($D_2O$): δ 1.15–1.76 (m, 16H), 3.25–3.38 (m, 1H), 3.40–3.51 (m, 1H), 3.52–3.80 (m, 3H), 4.06–4.18 (m, 1H), 4.23–4.35 (m, 2H), 4.42–4.55 (m, 2H), 4.65–4.80 (m, 1H). $^{31}P$ ($D_2O$, external $H_3PO_4$, broadband decoupled): 3.44, 4.11, and 4.75. FAB-MS m/q 845 [$C_{18}H_{29}O_{17}P_3K_6$ (M)], 807 [M-K+1H], 769 [M-2K+2H].

Preparation of crude porcine brain microsomes. The brain from an adult pig was homogenized (Polytron, setting 7 and 5 strokes) in ice-cold buffer A, consisting of 20 mM-Hepes/KOH, 110 mM-KCl, 10 mM-NaCl, 2 mM-MgCl2, 5 mM-KH2PO4, 2 mMEGTA, 1 mM-dithiothreitol (DTT), and 0.5 mM-p-toluenesulfonyl fluoride (PMSF). The homogenate was centrifuge at 500 g for 15 min at 4 oc, and the supernatant was pelleted by centrifugation at 35,000 g for 25 min. The pellet was resuspended in buffer B (as buffer A but without EGTA and PMSF). The washing procedure was repeated two times. The resulting final pellet was suspended in buffer B to a protein concentration of 2.1 mg/ml.

$Ca^{2+}$ release assay. Measurements of free $Ca^{2+}$ concentrations in incubation media were performed by using a $Ca^{2+}$-sensitive fluorescent dye, Fura-2, in a Hitachi F-2000 spectrofluorimeter. The assay medium consisted of 40 units of creatine kinase, 20 mM-creatine phosphate, 5 μg of oligomycin, and 0.5 μM-Fura 2 free acid in 2 ml of buffer B containing 0.4 mg of microsomal protein. The mixture were incubated for 5 min, and treated with 1 mM-ATP to allow the loading of $Ca^{2+}$ stores. Until the external $Ca^{2+}$ concentration returned to a near-base level, the microsomes were stimulated with the $Ca^{2+}$-mobilizing agents. Experiments were carried out at 37° C. Excitation and emission wavelengths were 340 and 510 nm, respectively. The fura-2 fluorescence ratio signal was calibrated, Grynkiewicz, G.; Poenie, M.; Tsien, R. Y., *J. Biol. Chem.*, 1985, 260, 3440.

Having described our invention, what we now claim is:
1. A compound of the structural formula:
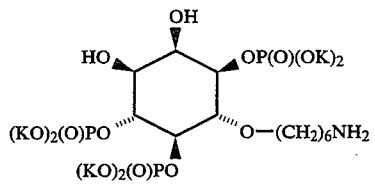
2. A compound of the structural formula:
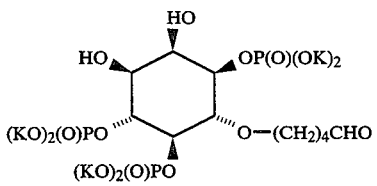
* * * * *